United States Patent

Suita et al.

(10) Patent No.: US 10,139,338 B2
(45) Date of Patent: Nov. 27, 2018

(54) ELECTROMECHANICAL TRANSDUCER

(71) Applicant: CANON KABUSHIKI KAISHA, Tokyo (JP)

(72) Inventors: Kenji Suita, Fujisawa (JP); Yousuke Takubo, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 775 days.

(21) Appl. No.: 14/591,508

(22) Filed: Jan. 7, 2015

(65) Prior Publication Data

US 2015/0211985 A1 Jul. 30, 2015

(30) Foreign Application Priority Data

Jan. 27, 2014 (JP) ................................ 2014-012007

(51) Int. Cl.
*G01N 21/17* (2006.01)
*B06B 1/02* (2006.01)
*G01N 29/24* (2006.01)
*H04R 19/00* (2006.01)

(52) U.S. Cl.
CPC ....... *G01N 21/1702* (2013.01); *B06B 1/0292* (2013.01); *G01N 29/2406* (2013.01); *G01N 29/2418* (2013.01); *H04R 19/00* (2013.01)

(58) Field of Classification Search
CPC ............... G01N 21/17; G01N 21/1702; G01N 29/2418; G01N 29/2406; H02N 1/00; H02N 1/08; B06B 1/0292; H04R 19/00
USPC ....................................................... 367/178
See application file for complete search history.

(56) References Cited

U.S. PATENT DOCUMENTS

| | | | | |
|---|---|---|---|---|
| 6,558,330 B1 * | 5/2003 | Ayter | ................... | B06B 1/0292 600/459 |
| 6,676,602 B1 * | 1/2004 | Barnes | ................ | G10K 11/346 600/443 |
| 7,443,765 B2 * | 10/2008 | Thomenius | .......... | B06B 1/0292 367/153 |
| 7,775,979 B2 * | 8/2010 | Thomenius | .......... | G01S 7/5208 600/437 |
| 9,525,121 B2 * | 12/2016 | Torashima | ......... | H01L 41/0815 |
| 2002/0130591 A1 * | 9/2002 | Fraser | .................. | B06B 1/0622 310/334 |

(Continued)

FOREIGN PATENT DOCUMENTS

WO 2008/136198 A1 11/2008

*Primary Examiner* — Isam A Alsomiri
*Assistant Examiner* — Amie M Ndure
(74) *Attorney, Agent, or Firm* — Fitzpatrick, Cella, Harper & Scinto

(57) ABSTRACT

Provided is an electromechanical transducer having a reduced unnecessary signal and improved acoustic characteristics. The electromechanical transducer includes an element. The element includes a plurality of cells that are two-dimensionally arranged and electrically connected. Each of the cells includes: a first electrode; and a vibrating film including a second electrode, the second electrode being opposed to the first electrode with a gap interposed therebetween. The cells are arranged so that, when center portions of the plurality of cells are connected by straight lines in all combinations, one of outermost straight lines and another of the outermost straight lines are non-parallel with each other or different in length of parallel portions.

16 Claims, 5 Drawing Sheets

(56) References Cited

U.S. PATENT DOCUMENTS

| | | | |
|---|---|---|---|
| 2005/0203404 A1* | 9/2005 | Freiburger | A61B 8/06 600/453 |
| 2005/0237858 A1* | 10/2005 | Thomenius | B06B 1/0292 367/155 |
| 2007/0016026 A1* | 1/2007 | Thomenius | G01S 7/5208 600/437 |
| 2007/0164632 A1* | 7/2007 | Adachi | A61B 8/4483 310/311 |
| 2008/0027323 A1* | 1/2008 | Freiburger | A61B 8/06 600/453 |
| 2008/0139946 A1* | 6/2008 | Adachi | A61B 8/4483 600/463 |
| 2010/0137719 A1* | 6/2010 | Ikeda | B06B 1/0292 600/459 |
| 2011/0115337 A1* | 5/2011 | Nakamura | G10K 9/122 310/334 |
| 2012/0256520 A1* | 10/2012 | Torashima | H01L 41/0815 310/300 |
| 2013/0018266 A1* | 1/2013 | Nishikubo | A61B 8/4483 600/443 |
| 2013/0063530 A1* | 3/2013 | Higashino | B41J 2/14233 347/71 |
| 2013/0069480 A1* | 3/2013 | Akiyama | H02N 11/00 310/300 |

* cited by examiner

ELECTROMECHANICAL TRANSDUCER

BACKGROUND OF THE INVENTION

Field of the Invention

The present invention relates to a capacitive transducer (Electromechanical Transducer) to be used as an ultrasound transducer.

Description of the Related Art

Hitherto, micromechanical members to be manufactured using micromachining technology may be processed on the order of micrometers, and various functional microelements are realized using such micromechanical members. An electromechanical transducer using such technology is being researched as an alternative to a transducer using a piezoelectric element. With such an electromechanical transducer, an acoustic wave (hereinafter sometimes represented by ultrasonic wave) may be transmitted or received using vibrations of a vibrating film, and in particular, excellent broadband characteristics in a liquid may be obtained with ease. Note that, the "acoustic wave" as used herein encompasses waves called a sonic wave, an ultrasonic wave, and a photoacoustic wave. For example, the "acoustic wave" encompasses a photoacoustic wave generated in a test object when the inside of the test object is irradiated with light (electromagnetic wave) such as visible light or infrared light.

Regarding the above-mentioned technology, there is known an electromechanical transducer exists that is formed of cells two-dimensionally arranged at regular intervals. Each of the cells includes a vibrating film and two electrodes opposed to each other with a gap interposed therebetween. Further, there is known an electromechanical transducer in which corrugated cells are two-dimensionally arranged or an electromechanical transducer in which means for blocking a signal is provided in an outer peripheral portion (see International Publication No. 2008/136198).

An output of an electromechanical transducer is determined depending on a sum of signals of time-varying interelectrode distances of a plurality of cells sharing a signal extraction electrode. Thus, the output is correlated with a sum of vibration velocities of a plurality of vibrating films. In the case of an electromechanical transducer having an infinite size, the vibration velocity of the vibrating film is uniform with regard to all the cells, and no unnecessary signal is generated. However, when cells that form an electromechanical transducer having a finite size are two-dimensionally arranged, a cell in an outer peripheral portion and a cell in a center portion of the electromechanical transducer have different boundary conditions. Therefore, when a plane wave enters the transducer, the vibration velocity of the vibrating film differs between the cell in the outer peripheral portion and the cell in the center portion. Such difference in vibration velocity of the vibrating films prevents uniformity of the vibration velocities of the vibrating films in the electromechanical transducer. Distribution of the cells with non-uniform vibration velocities of the vibrating films changes over time due to interaction between the cells.

The change over time is described with reference to FIGS. 5A to 5D. FIG. 5A is a graph showing a relationship between time and output. FIG. 5B, FIG. 5C, and FIG. 5D are sectional views illustrating vibration velocity distribution of vibrating films of an electromechanical transducer. Velocity of each of the cells in one element 1 in the electromechanical transducer is denoted by a reference numeral 2. First, when a plane wave enters the electromechanical transducer, due to difference in boundary condition, a section of vibration velocity distribution of the vibrating films is as illustrated in FIG. 5B. Next, due to interaction between the cells, it is seen that positions of cells that include the vibrating films having a high vibration velocity in FIG. 5B travel toward opposed sides, respectively, as illustrated in FIG. 5C. In this case, cells that include the vibrating films having positive and negative vibration velocities that are the same in magnitude exist in the electromechanical transducer, and thus, the output is small (see around t2 in FIG. 5A). Finally, the positions of cells having the high vibration velocity in the vibration velocity distribution that is seen to travel toward the opposed sides reach the opposed sides as illustrated in FIG. 5D, and thus, the absolute value of the sum of the vibration velocities of the vibrating films in the electromechanical transducer becomes large (see around t3 in FIG. 5A). When the absolute value of the sum of the vibration velocities of the vibrating films becomes large, an unnecessary signal is generated, which makes it difficult to obtain a high quality image.

In the technology disclosed in International Publication No. 2008/136198, in order to reduce non-uniformity in vibration velocity of the vibrating films in the electromechanical transducer, an electromechanical transducer having a signal blocking portion is used. However, when such a signal blocking portion is provided, a ratio of cells from which an output can be taken out in the electromechanical transducer is reduced, and transmitting or receiving sensitivity thereof is liable to be reduced.

SUMMARY OF THE INVENTION

In view of the above-mentioned problems, according to one embodiment of the present invention, there is provided an electromechanical transducer, including an element, the element including a plurality of cells that are two-dimensionally arranged and electrically connected, each of the plurality of cells including: a first electrode; and a vibrating film including a second electrode, the second electrode being opposed to the first electrode with a gap interposed therebetween. The plurality of cells are arranged so that, when center portions of the plurality of cells are connected by straight lines in all combinations, one outermost straight line and another outermost straight line are one of non-parallel with each other and different in length of parallel portions.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

In an electromechanical transducer according to the present invention, when center portions of a plurality of cells are connected by straight lines in all combinations, a plurality of outermost straight lines are not in parallel with each other or different in length of parallel portions. In other words, the plurality of cells are arranged in the above-mentioned manner. Typically, the plurality of cells are formed so as to have the same frequency characteristics. This causes timing of unnecessary signal generation to differ, and thus, an unnecessary signal due to difference in boundary condition of the cells is reduced. Further, a signal blocking portion is not provided in the electromechanical transducer, and thus, cells can be densely arranged in the electromechanical transducer.

Figure 1A:
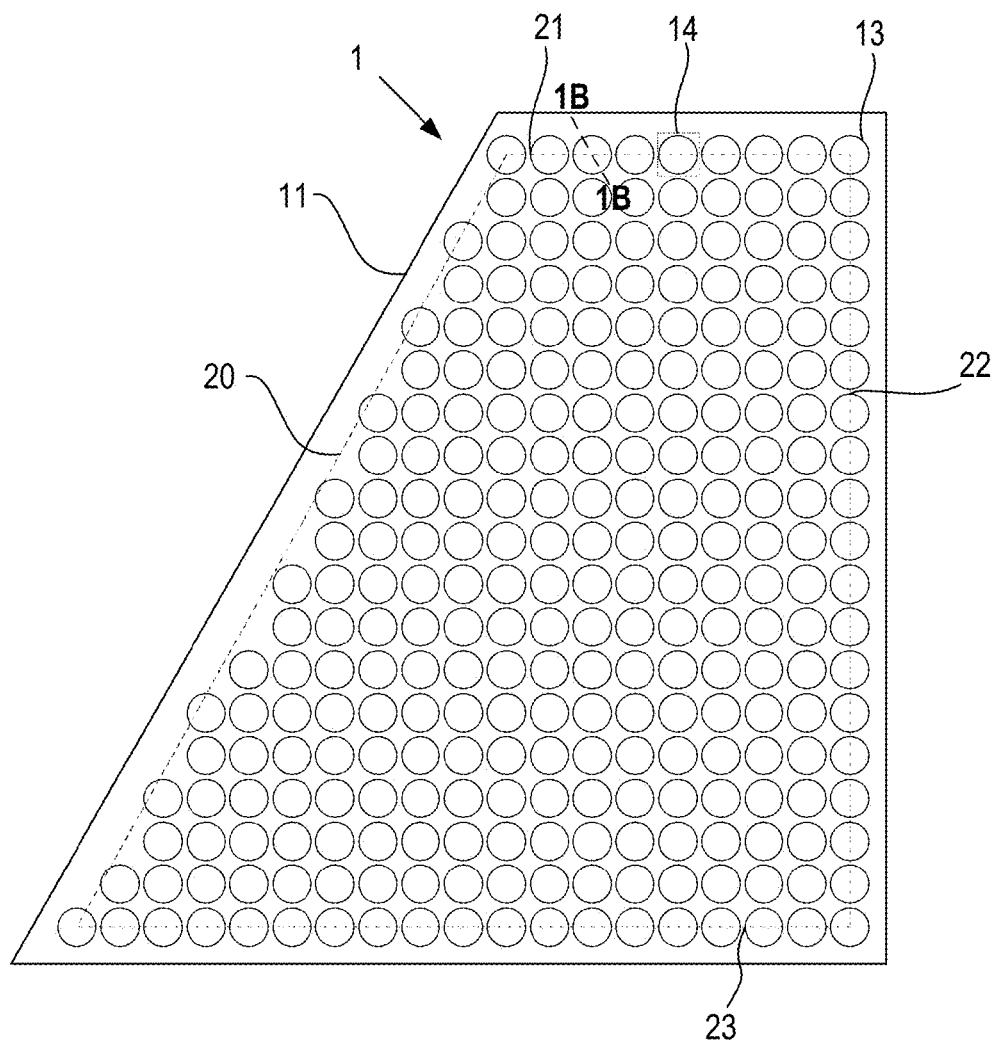
FIG. 1A is a top view of an exemplary electromechanical transducer according to the present invention.
Figure 1B:
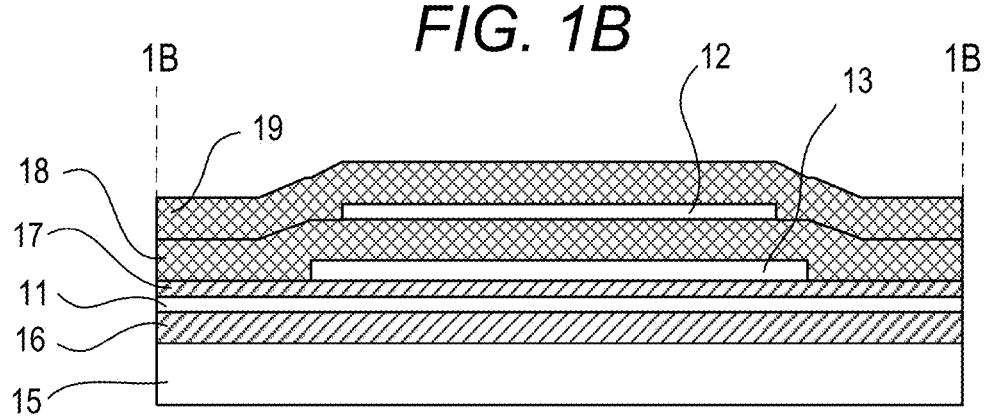
FIG. 1B is a sectional view of the exemplary electromechanical transducer according to the present invention taken along the line 1B-1B of FIG. 1A.

An embodiment of the present invention is described in the following with reference to FIG. 1A and FIG. 1B. FIG. 1A is a top view of an element 1 of an electromechanical transducer of this embodiment, and FIG. 1B is a sectional view taken along the line 1B-1B of FIG. 1A. In the element 1 of the electromechanical transducer of this embodiment, a distance between closest adjacent cells is fixed. In FIG. 1A, a plurality of cells 14 are two-dimensionally arranged at regular intervals (specifically, the distance between closest adjacent cells is the same). Note that, "a distance between cells is fixed" and "a distance between cells is the same" as used herein not only include a case in which the distance between the cells is strictly the same with regard to all the cells but also include a case in which there is an error, but change in vibration velocity can be regarded as the same in the element. First electrodes or second electrodes of the cells are electrically connected, respectively, that is, are wired together. In FIG. 1A, 256 cells are included, but the number of the cells is not limited thereto insofar as the cells are two-dimensionally arranged at regular intervals. Further, all the cells in the element 1 of the electromechanical transducer are formed so as to have substantially the same width and substantially the same thickness. In other words, all the cells are formed so as to have the same frequency characteristics. Note that, "have the same frequency characteristics" as used herein not only includes a case in which the frequency characteristics of the cells in the element are strictly the same but also includes a case in which there is an error such as film formation variations, but the cells can be regarded as responding to the same ultrasonic wave or the same output signal with the same frequency-dependent intensity distribution (the same frequency characteristics). In this embodiment, the cells are two-dimensionally arranged. With regard to outermost straight lines 20, 21, 22, and 23, the straight line 21 is not in parallel with the straight lines 20 and 22, but is in parallel with the straight line 23. Further, the straight lines 21 and 23 are different in length of parallel portions. Specifically, the plurality of cells 14 are arranged so that, when center portions of the plurality of cells are connected by straight lines in all combinations, one outermost straight line and another outermost straight line are not in parallel with each other or different in length of parallel portions. In particular, the cells are arranged so that an outermost straight line and another outermost straight line that intersects a normal to the one outermost straight line are not in parallel with each other or different in length of parallel portions. For example, the straight line 23 is in parallel with the straight line 21 that intersects a normal to the straight line 23, but the straight lines 23 and 21 are different in length of parallel portions. The straight line 23 may not be parallel with the straight line 21.

Figure 5A:
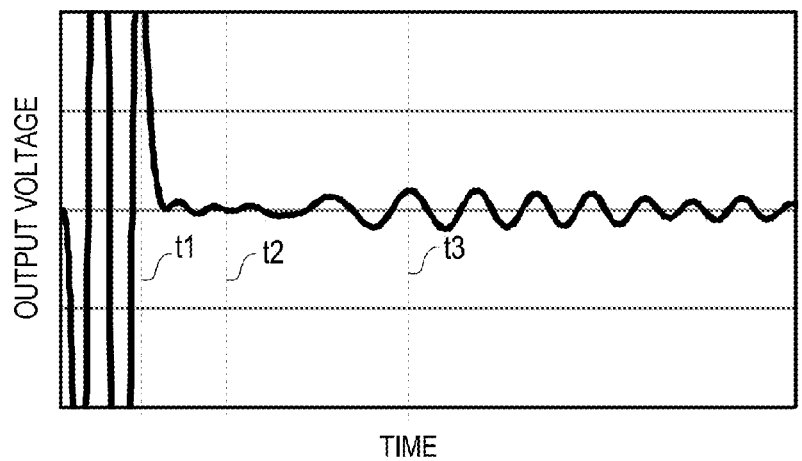
FIG. 5A is a graph showing a relationship between output and time when a plane wave is received.
Figure 5B:
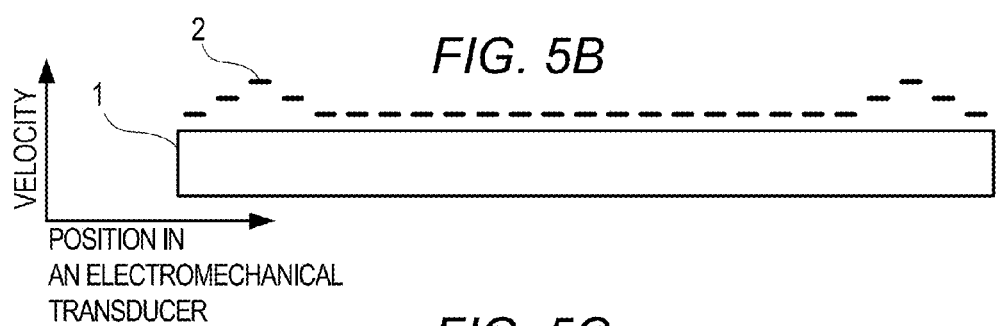
FIG. 5B is a diagram illustrating change over time in vibration velocity distribution of vibrating films when a plane wave is received (at t1).
Figure 5C:
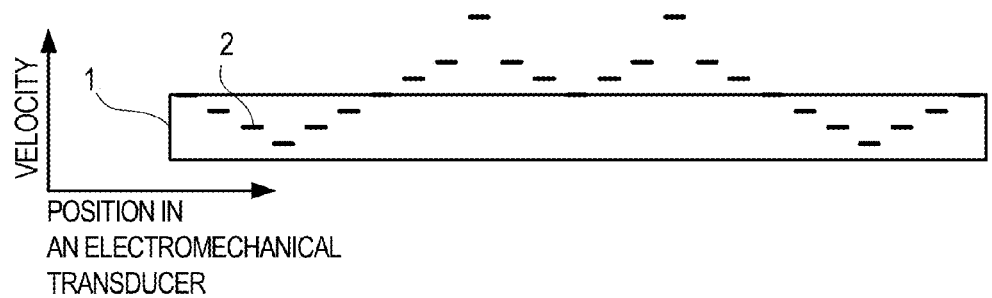
FIG. 5C is a diagram illustrating change over time in vibration velocity distribution of the vibrating films when the plane wave is received (at t2).
Figure 5D:
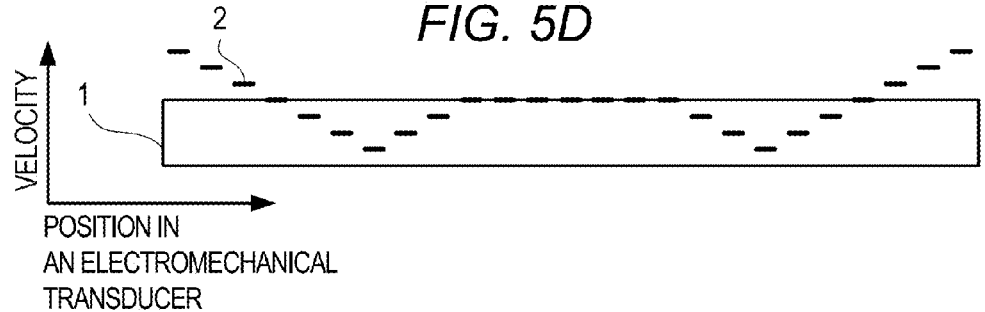
FIG. 5D is a diagram illustrating change over time in vibration velocity distribution of the vibrating films when the plane wave is received (at t3).

In the element 1 of the electromechanical transducer of this embodiment, as described above, the cells are arranged so that a distance from one outermost cell to an opposed outermost cell is not fixed. Therefore, a time period necessary for change in vibration velocity distribution of the vibrating films to reach an opposed side (see FIG. 5D) differs depending on a position in the section, and thus, a sum of vibration velocities of the vibrating films only changes gradually. This reduces a ratio of an unnecessary signal to a main signal.

As illustrated in FIG. 1B, in the cell 14 of this embodiment, a first electrode 11 is formed on a first insulating film 16 formed on a substrate 15. Further, a vibrating film including a second electrode 12 is vibratably supported by a vibrating film support portion. The vibrating film is provided over a second insulating film 17 on the first electrode 11 on a side opposite to the substrate with a gap (cavity) 13 interposed therebetween. When the substrate 15 is an insulating substrate, the first insulating film 16 may be omitted. Further, the vibrating films illustrated in FIG. 1A are in the shape of a circle, but may be in the shape of a square, a rectangular, or the like. The first electrode 11 (or the second electrode 12) is used as an electrode for applying a bias voltage, or, an electrode for applying an electric signal or for taking out an electric signal. An electrode for applying a bias voltage may be shared by a plurality of elements. On the other hand, an electrode for taking out an electric signal or for applying an electric signal of an element is required to be electrically separated from other such electrodes of other elements.

A first membrane layer 18 and a second membrane layer 19 that form the vibrating film are insulating films. A silicon nitride film can be formed with a low tensile stress and deformation to a large extent of the vibrating film due to a residual stress of the silicon nitride film can be prevented, and thus, a silicon nitride film is particularly desired as the membrane layers 18 and 19. The membrane layers 18 and 19 that form the vibrating film are not necessarily required to be insulating films. When the membrane layers are not insulating films, the membrane layers may be used as the second electrode.

The electromechanical transducer according to the present invention may be manufactured by any method. A manufacturing method according to an embodiment of the present invention is described with reference to FIG. 2A to FIG. 2F. FIG. 2A to FIG. 2F are sectional views illustrating manufacturing steps of the electromechanical transducer. FIG. 2A to FIG. 2F are sectional views illustrating a portion corresponding to the sectional view of FIG. 1B taken along the line 1B-1B of FIG. 1A.

Figure 2A:
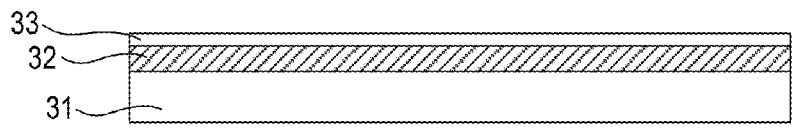
FIG. 2A is a first sectional view illustrating a method of manufacturing the electromechanical transducer according to the present invention.

As illustrated in FIG. 2A, a first insulating film 32 is formed on a substrate 31. The substrate 31 is a silicon substrate, and the first insulating film 32 is formed for the purpose of establishing insulation from a first electrode 33. It is desired that the substrate 31 be a substrate having a small surface roughness. When the surface roughness is large, the surface roughness is transferred during a film forming process subsequent to this step, and thus, a distance between the first electrode and a second electrode 37 varies among the cells or among the elements. Such variations lead to variations in transmitting and receiving sensitivities. Then, the first electrode 33 is formed on the first insulating film 32. It is desired that the first electrode 33 be formed of a conductive material having a small surface roughness. Similarly to the case of the substrate 31, when the surface roughness of the first electrode 33 is large, the interelectrode distance between the first electrode 33 and the second electrode 37 varies among the cells or among the elements.

Figure 2B:
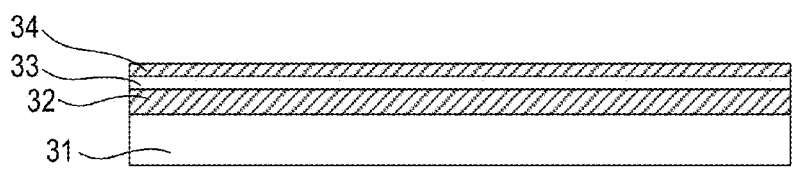
FIG. 2B is a second sectional view illustrating the method of manufacturing the electromechanical transducer according to the present invention.

Then, as illustrated in FIG. 2B, a second insulating film 34 is formed on the first electrode 33. The second insulating film 34 is formed for the purpose of preventing an electrical short circuit or dielectric breakdown when a voltage is applied between the first electrode 33 and the second electrode 37. Another purpose of forming the second insulating film 34 is to prevent the first electrode 33 from being etched when a sacrificial layer is removed subsequently to this step. When the electromechanical transducer is to be driven with a low voltage, the membranes are insulating, and the first electrode is not etched by an etchant or an etching gas used when the sacrificial layer is removed, the second insulating film is not necessarily required to be formed. Similarly to the case of the substrate 31, when the surface roughness of the second insulating film 34 is large, the interelectrode distance between the first electrode and the second electrode varies among the cells, and thus, an insulating film having a small surface roughness is desired as the second insulating film 34. Such a film that is desired as the second insulating film 34 is, for example, a silicon nitride film or a silicon oxide film.

Figure 2C:
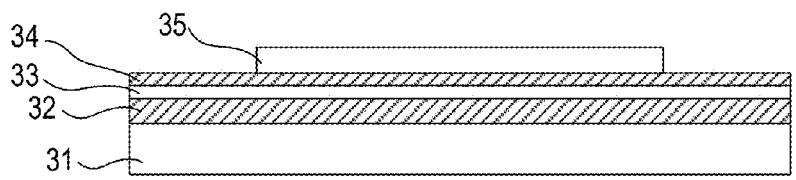
FIG. 2C is a third sectional view illustrating the method of manufacturing the electromechanical transducer according to the present invention.

Then, as illustrated in FIG. 2C, a sacrificial layer 35 is formed. As the sacrificial layer 35, a material having a small surface roughness is desired. Similarly to the case of the substrate 31, when the surface roughness of the sacrificial layer is large, the distance between the first electrode and the second electrode varies among the cell, and thus, a sacrificial layer having a small surface roughness is desired as the sacrificial layer 35. Further, for the purpose of shortening an etching time for etching out the sacrificial layer, as the sacrificial layer material, a material having a high etching velocity is desired. Further, such a sacrificial layer material is required with which the second insulating film 34, a first membrane layer 36 to be described later, and the second electrode 37 to be described later are hardly etched by the etchant or the etching gas for removing the sacrificial layer 35. If the second insulating film, the first membrane layer, and the second electrode are etched by the etchant or the etching gas for removing the sacrificial layer, a thickness of the vibrating film and a distance between the first electrode and the second electrode vary, which lead to variations among the cells. With regard to the sacrificial layer material, when the first membrane layer is a silicon nitride film or a silicon oxide film, chromium is desired, which has a small surface roughness and can be etched by an etchant that does not etch the second electrode and the first membrane layer.

Figure 2D:
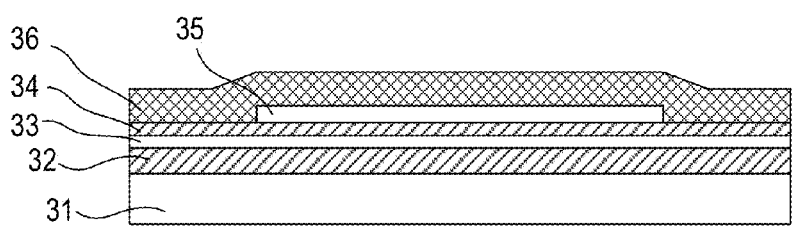
FIG. 2D is a fourth sectional view illustrating the method of manufacturing the electromechanical transducer according to the present invention.

Then, as illustrated in FIG. 2D, the first membrane layer 36 is formed on the sacrificial layer. It is desired that the first membrane layer 36 has a low tensile stress. For example, it is desired that the tensile stress be 300 MPa or less. A stress on a silicon nitride film is controllable, and can be set to a low tensile stress of 300 MPa or less. When the first membrane layer has a compressive stress, sticking or buckling of the first membrane layer is caused to greatly deform the vibrating film to be described later. Further, when the first membrane layer has a large tensile stress, the first membrane layer may be broken. Therefore, it is desired that the first membrane layer have a low tensile stress.

Figure 2E:
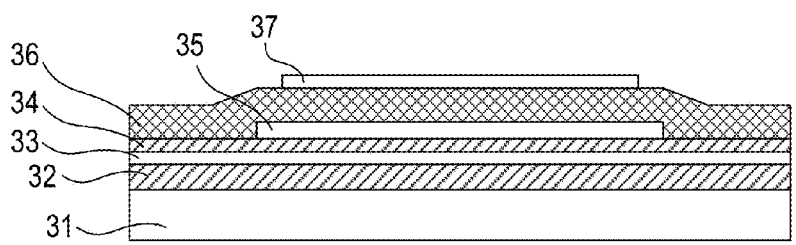
FIG. 2E is a fifth sectional view illustrating the method of manufacturing the electromechanical transducer according to the present invention.

Then, as illustrated in FIG. 2E, the second electrode 37 is formed on the first membrane layer 36, and further, an etching hole (not shown) is formed in the first membrane layer. After that, the sacrificial layer 35 is removed through the etching hole. It is desired that a material of the second electrode 37 have a small residual stress and heat resistance. When the second electrode has a large residual stress, the vibrating film is deformed to a large extent, and thus, it is desired that the second electrode have a small residual stress. Further, when the second electrode does not have heat resistance, depending on a temperature when the second membrane layer to be described later or a sealing layer for forming a sealing portion for sealing the etching hole is formed or the like, change in quality or increase in stress may be caused. Thus, a material that does not cause those phenomena is desired. Further, when the sacrificial layer is removed with the second electrode being exposed, it is necessary to remove the sacrificial layer under a state in which a photoresist for protecting the second electrode or the like is applied. In such a case, sticking of the first membrane layer is liable to occur due to a stress of the photoresist or the like. Therefore, it is desired that the second electrode have etching resistance so that the sacrificial layer can be removed with the second electrode being exposed without a photoresist. Exemplary materials of the second electrode include titanium and an aluminum-silicon alloy. Sticking is a phenomenon that, after the sacrificial layer is removed, the vibrating film as a structure sticks to a bottom of the cavity.

Figure 2F:
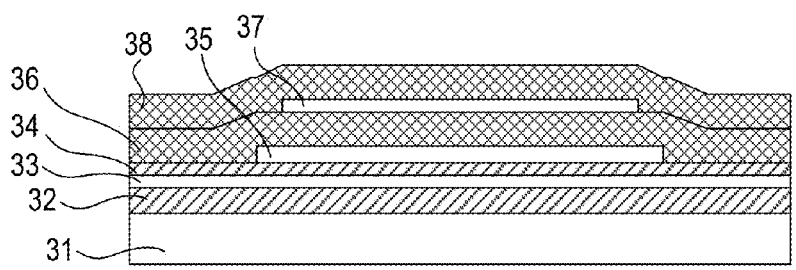
FIG. 2F is a sixth sectional view illustrating the method of manufacturing the electromechanical transducer according to the present invention.

Then, as illustrated in FIG. 2F, a second membrane layer 38 is formed. In this step, not only the second membrane layer but also the sealing portion for sealing the etching hole is formed. By forming the second membrane layer, the sealing portion can be formed together with formation of the vibrating film having a desired spring constant. When a step of sealing the etching hole and a step of forming the second membrane layer are the same single step as this step, the vibrating film can be formed only by a film forming step. Therefore, the thickness of the vibrating film is easy to control, and variations in the spring constant or variations in deflection of the vibrating film due to variations in the thickness can be controlled. Therefore, variations in the receiving or transmitting sensitivity among the cells or among the elements can be reduced.

The step of sealing the etching hole and the step of forming the second membrane layer may be separate from each other. The sealing portion may be formed after the second membrane layer is formed, or, the second membrane layer may be formed after the sealing portion is formed. Further, it is desired that a material of the second membrane layer 38 have a low tensile stress. Similarly to the case of the first membrane layer, when the second membrane layer has a compressive stress, sticking or buckling of the second membrane layer may be caused, leading to deformation to a large extent. Further, when the second membrane layer has a large tensile stress, the second membrane layer may be broken. Therefore, it is desired that the second membrane layer have a low tensile stress. A stress on a silicon nitride film is controllable, and can be set to a low tensile stress of 300 MPa or less. In a step (not shown) subsequent to this step, wiring for connecting the first electrode 33 to another portion and connecting the second electrode 37 to another portion is formed. As a material of the wiring, aluminum or the like may be used.

The present invention is described in detail through description of more specific examples.

EXAMPLE 1

Example 1 of the present invention is described with reference to FIG. 1A. FIG. 1A is a top view of an electromechanical transducer of Example 1. The electromechanical transducer of Example 1 is formed of the plurality of cells 14 each of which has the shape of a square and which are arranged so that a minimum distance between the centers of the cells is 45 μm. In FIG. 1A, the electromechanical transducer includes 256 cells, but the number of the cells is not limited thereto insofar as the cells are two-dimensionally arranged at regular intervals. Further, all the cells in the element have widths, thicknesses, film thicknesses, residual stresses, and the like, which can be regarded as the same, respectively. In other words, all the cells have the same frequency characteristics.

Further, the outermost straight lines 20, 21, 22, and 23 form a trapezoid. The straight line 21 and the straight line 23 that are in parallel with and opposed to each other are different in length (for example, the shorter side is 40% to 50% of the longer side in length), and the straight line 22 and the straight line 23 that form a right angle are the same in length. The outermost straight lines in Example 1 form a trapezoid, but may form a triangle. When the formed shape is a trapezoid or a triangle, a plurality of elements can be arranged tightly to form the electromechanical transducer. Therefore, a plurality of elements can be arranged densely in a predetermined region to obtain a high quality image. Further, the vibrating films of Example 1 in plane are in the shape of a circle, but may be in the shape of a square, a hexagon, or the like. When the shape is a circle, vibration of the vibrating films in an unnecessary vibration mode can be inhibited. Further, the cells, which form the element of the electromechanical transducer, share the electrode for applying a bias voltage and the electrode for taking out a signal.

This structure causes a distance between a center of a cell on an outermost straight line and a center of a cell on another outermost straight line intersecting the normal to the outermost straight line to be non-uniform, and thus, an unnecessary signal can be reduced. For example, compared with a case in which an element having the same size as that of Example 1 is formed by cells that have the same structure, the same number of the cells, and the same center-to-center distance of the cells as those of Example 1 but are arranged so that outermost straight lines form a square, a ratio of an unnecessary signal to a main signal can be reduced by about 30%.

EXAMPLE 2

Figure 3:
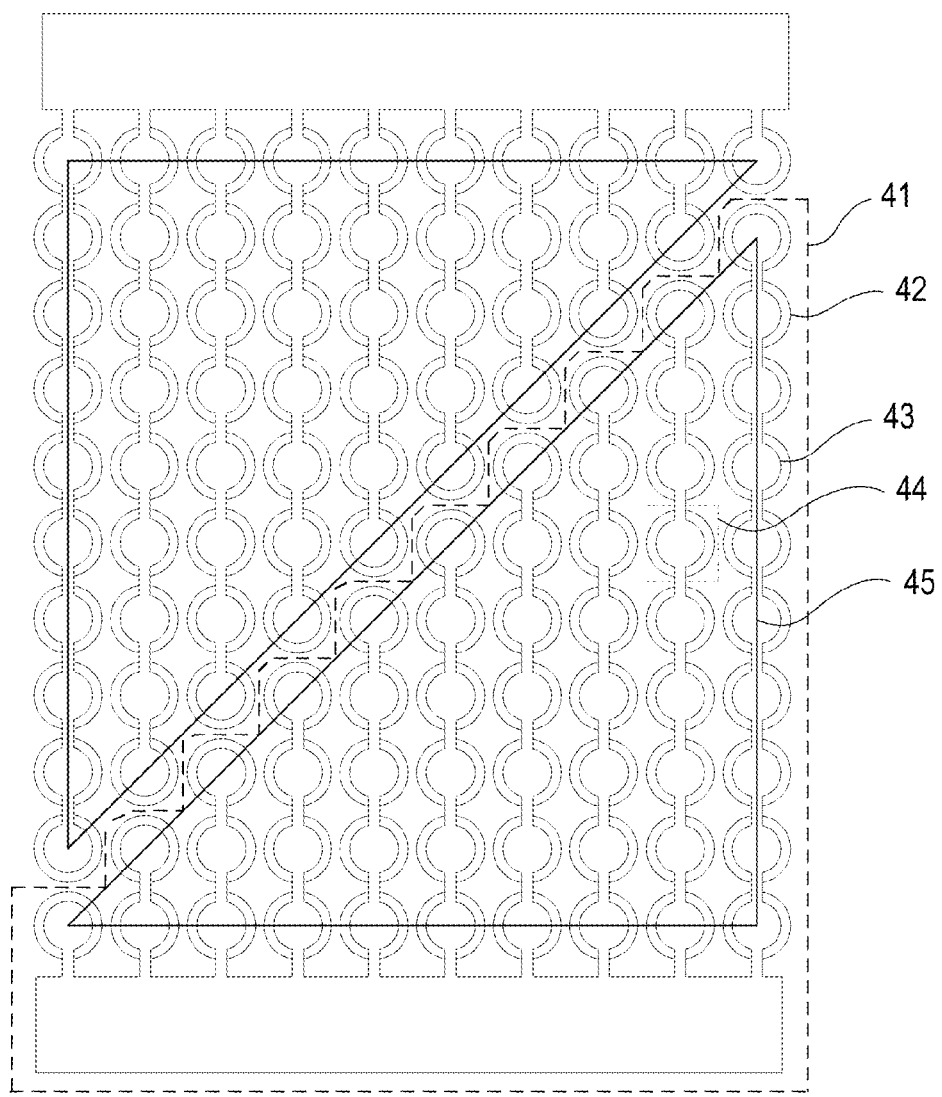
FIG. 3 is a top view of another exemplary electromechanical transducer according to the present invention.

A structure of an electromechanical transducer according to Example 2 of the present invention is described with reference to FIG. 3. FIG. 3 is a top view in which identical two elements are arranged. An element 41 of Example 2 is formed of a plurality of cells 44 that are arranged in the shape of a square in which a center-to-center distance of the cells is 45 μm. Further, all the cells in the elements have widths, thicknesses, and the like, which can be regarded as the same. Outermost straight lines 45 form a triangle. Note that, the cell includes a cell gap 42 and a second electrode 43.

The outermost straight lines that are not in parallel with one another form a triangle, and thus, a time period necessary for change in vibration velocity distribution of the vibrating films that is caused at three sides of the triangle to reach an opposed side differs to reduce an unnecessary signal. Further, the cells can be arranged with smaller gaps, and thus, the cells can be arranged densely in a predetermined region so that a high quality image can be obtained. By combining the two elements in each of which the outermost straight lines form a triangle so that hypotenuses thereof are opposed to each other as illustrated in FIG. 3, compared with a case in which the cells have the same frequency characteristics and the same number and density of the cells as those of this embodiment but the outermost straight lines form a rectangle, a ratio of an unnecessary signal to a main signal can be reduced.

EXAMPLE 3

Figure 4A:
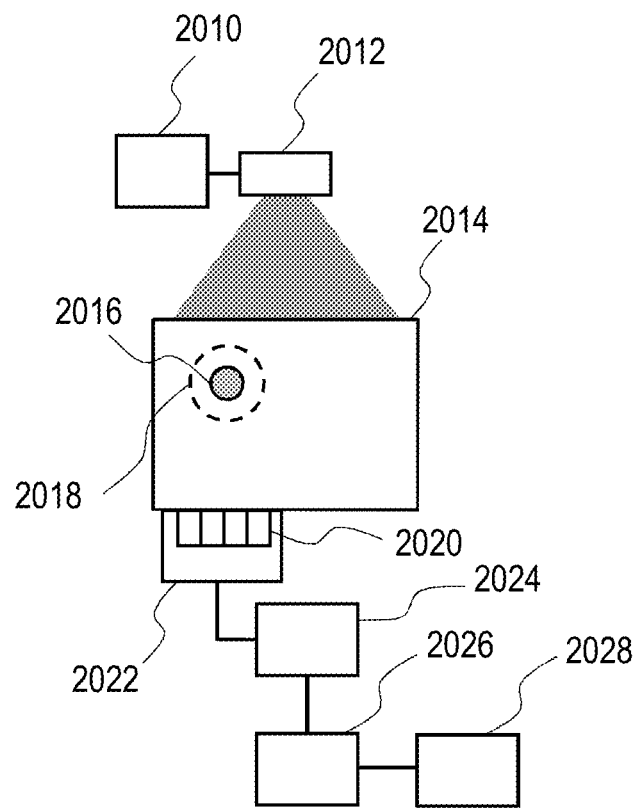
FIG. 4A is an explanatory diagram of an exemplary information acquiring device using the electromechanical transducer according to the present invention.

FIG. 4A illustrates a test object information acquiring device using a photoacoustic effect according to Example 3 of the present invention. Pulsed light emitted from a light source 2010 irradiates a test object 2014 via an optical member 2012 such as a lens, a mirror, or an optical fiber. A light absorber 2016 inside the test object 2014 absorbs energy of the pulsed light to generate a photoacoustic wave 2018 as an acoustic wave. An electromechanical transducer 2020 of the present invention in a probe 2022 receives the photoacoustic wave 2018 to convert the photoacoustic wave 2018 into an electric signal, and outputs the electric signal to a signal processor 2024. The signal processor 2024 subjects the input electric signal to signal processing such as A/D conversion and amplification, and outputs the resultant signal to a data processor 2026. The data processor 2026 uses the input signal to acquire test object information (characteristics information that reflects an optical property value of the test object, such as a light absorption coefficient) as image data. Here, the signal processor 2024 and the data processor 2026 are collectively referred to as a processor. A display unit 2028 displays an image based on the image data input from the data processor 2026. As described above, the test object information acquiring device of this embodiment includes the electromechanical transducer of the present invention, the light source, and the processor. The transducer receives a photoacoustic wave generated when the light emitted from the light source irradiates the test object and converts the photoacoustic wave into an electric signal, and the processor acquires the information on the test object through use of the electric signal.

Figure 4B:
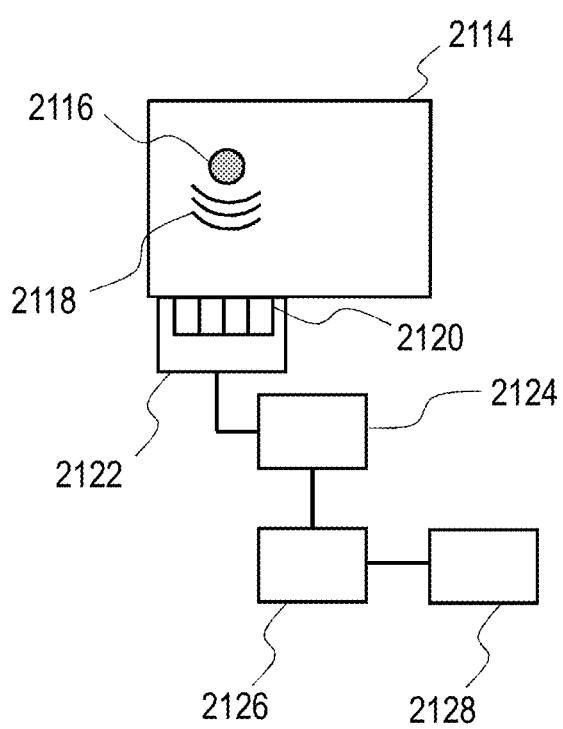
FIG. 4B is an explanatory diagram of another exemplary information acquiring device using the electromechanical transducer according to the present invention.

FIG. 4B illustrates a test object information acquiring device such as an ultrasonic echo diagnosis apparatus using the reflection of an acoustic wave. An acoustic wave transmitted from an electromechanical transducer 2120 of the present invention in a probe 2122 to a test object 2114 is reflected by a reflector 2116. The transducer 2120 receives a reflected acoustic wave (reflected wave) 2118 to convert the reflected acoustic wave 2118 into an electric signal, and outputs the electric signal to a signal processor 2124. The signal processor 2124 subjects the input electric signal to signal processing such as A/D conversion and amplification and outputs the resultant signal to a data processor 2126. The data processor 2126 uses the input signal to acquire test object information (characteristics information that reflects a difference in acoustic impedance) as image data. Here, the signal processor 2124 and the data processor 2126 are also collectively referred to as a processor. A display unit 2128 displays an image based on the image data input from the data processor 2126. As described above, the test object information acquiring device of this embodiment includes the electromechanical transducer of the present invention, and the processor for acquiring the information on the test object through use of the electric signal output from the transducer. The transducer receives the acoustic wave from the test object and outputs an electric signal.

Note that, the probe may be configured to scan mechanically or may be configured to be moved by a user, such as a doctor or an engineer, relative to the test object (handheld type). In the case of the test object information acquiring device using a reflected wave as illustrated in FIG. 4B, a probe for transmitting an acoustic wave may be provided separately from a probe for receiving the acoustic wave. Further, the test object information acquiring device may have both the functions of the devices of FIGS. 4A and 4B so as to acquire both the test object information that reflects an optical property value of a test object and test object information that reflects a difference in acoustic impedance. In this case, the transducer 2020 of FIG. 4A may transmit an acoustic wave and receive a reflected wave instead of merely receiving a photoacoustic wave.

The electromechanical transducer according to one embodiment of the present invention has the structure described above, and thus the distance between the outermost straight lines opposed to each other is not uniform, or has a non-uniform portion. Therefore, a time period in which the change in vibration velocity distribution of the vibrating films is repeated between the outermost cells is at least partly non-uniform. This causes the timing of unnecessary signal generation to differ between at least a part of the outermost cells, and thus, the unnecessary signal due to difference in boundary condition can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-012007, filed Jan. 27, 2014, which is hereby incorporated by reference herein in its entirety.

What is claimed is:

1. An electromechanical transducer, comprising;
a substrate; and
an element disposed on or over a surface of the substrate, the element comprising a plurality of cells that are two-dimensionally arranged and electrically connected,
each of the plurality of cells comprising:
a first electrode; and
a vibrating film comprising a second electrode, the second electrode being opposed to the first electrode with a gap interposed therebetween,
wherein the first electrodes of the plurality of cells are electrically connected within the element,
wherein the second electrodes of the plurality of cells are electrically connected within the element, and
wherein the plurality of cells are arranged so that, when the cells are viewed from a direction normal to the surface of the substrate, center portions of the plurality of cells are connected by straight lines in all combinations, and one outermost straight line connecting the center portions of a first group of the plurality of cells and another outermost straight line connecting center portions of a second group of the plurality of cells are one of non-parallel with each other and different in length of parallel portions.

2. An electromechanical transducer according to claim 1, wherein the plurality of cells have the same frequency characteristics.

3. An electromechanical transducer according to claim 1, wherein the each of the plurality of cells comprises:
a substrate;
the first electrode formed on one surface side of the substrate;
the vibrating film including the second electrode opposed to the first electrode, and a membrane; and
a vibrating film support portion configured to support the vibrating film so that a gap is formed between the first electrode and the vibrating film.

4. An electromechanical transducer according to claim 1, wherein the outermost straight lines form a trapezoid.

5. An electromechanical transducer according to claim 4, wherein, among the outermost straight lines forming the trapezoid, two straight lines that form a right angle are the same in length, and straight lines that are in parallel with and opposed to each other have a shorter side and a longer side, the shorter side being 40% to 50% of the longer side in length.

6. An electromechanical transducer according to claim 1, wherein the outermost straight lines form a triangle.

7. An electromechanical transducer according to claim 1, wherein the outermost straight lines comprise two straight lines that form a right angle.

8. A test object information acquiring device, comprising:
the electromechanical transducer according to claim 1; and
a processor configured to acquire information on a test object through use of an electric signal output from the electromechanical transducer,
the electromechanical transducer being configured to receive an acoustic wave from the test object and convert the acoustic wave into the electric signal.

9. A test object information acquiring device according to claim 8, further comprising a light source,
wherein the electromechanical transducer receives a photoacoustic wave that is generated when a test object is irradiated with light emitted from the light source, and converts the photoacoustic wave into an electric signal, and
wherein the processor uses the electric signal to acquire information on the test object.

10. An electromechanical transducer, comprising;
a substrate; and
an element disposed on or over a surface of the substrate, the element comprising a plurality of cells that are two-dimensionally arranged and electrically connected, each of the plurality of cells comprising:
- a first electrode; and
- a vibrating film comprising a second electrode, the second electrode being opposed to the first electrode with a gap interposed therebetween, wherein the first electrode of the plurality of cells are electrically connected within the element, wherein the second electrode of the plurality of cells are electrically connected within the element, and wherein outermost straight lines of the element form a trapezoid.

11. An electromechanical transducer according to claim 10, wherein the plurality of cells have the same frequency characteristics.

12. An electromechanical transducer according to claim 10, wherein the each of the plurality of cells comprises:
- a substrate;
- the first electrode formed on one surface side of the substrate;
- the vibrating film including the second electrode opposed to the first electrode, and a membrane; and
- a vibrating film support portion configured to support the vibrating film so that a gap is formed between the first electrode and the vibrating film.

13. An electromechanical transducer according to claim 10, wherein, among the outermost straight lines forming the trapezoid, two straight lines that form a right angle are the same in length, and straight lines that are in parallel with and opposed to each other have a shorter side and a longer side, the shorter side being 40% to 50% of the longer side in length.

14. An electromechanical transducer according to claim 10, wherein the outermost straight lines comprise two straight lines that form a right angle.

15. A test object information acquiring device, comprising:
- the electromechanical transducer according to claim 10; and
- a processor configured to acquire information on a test object through use of an electric signal output from the electromechanical transducer,
- the electromechanical transducer being configured to receive an acoustic wave from the test object and convert the acoustic wave into the electric signal.

16. A test object information acquiring device according to claim 15, further comprising a light source, wherein the electromechanical transducer receives a photoacoustic wave that is generated when a test object is irradiated with light emitted from the light source, and converts the photoacoustic wave into an electric signal, and wherein the processor uses the electric signal to acquire information on the test object.

\* \* \* \* \*